United States Patent [19]

Mooney et al.

[11] Patent Number: 4,477,890

[45] Date of Patent: Oct. 16, 1984

[54] MAPPING DISC DEFECT DETECTOR

[75] Inventors: Donald G. Mooney, Orange; Ludwig Ceshkovsky, Fountain Valley, both of Calif.

[73] Assignee: Discovision Associates, Costa Mesa, Calif.

[21] Appl. No.: 353,740

[22] Filed: Mar. 1, 1982

[51] Int. Cl.$^3$ ............... H04N 5/76; G01N 21/32; G11B 27/36
[52] U.S. Cl. ............................. 369/53; 369/54; 369/58; 358/342
[58] Field of Search .................. 358/342; 369/53, 54, 369/55, 56, 58, 272, 275; 356/345, 371, 376, 432, 444, 445, 237

[56] References Cited

U.S. PATENT DOCUMENTS

| | | | |
|---|---|---|---|
| 4,030,835 | 6/1977 | Firester et al. | 369/54 X |
| 4,069,484 | 1/1978 | Firester et al. | 369/54 X |
| 4,307,419 | 12/1981 | Matey et al. | 369/54 X |
| 4,325,134 | 4/1982 | Langley et al. | 369/53 X |

Primary Examiner—Robert L. Richardson
Attorney, Agent, or Firm—Ronald J. Clark

[57] ABSTRACT

Apparatus for generating a map of detectable characteristics of a disc. A scanning signal display device has a detector coupled to the intensity input thereof. The detector detects the characteristics at a location on the disc which is scanned in a spiral pattern and provides a signal representative of the detected characteristics to the display device. A signal is generated and provided to the drive inputs of the display device to cause the trace of the device to follow a spiral pattern corresponding to the scan pattern of the predetermined location.

5 Claims, 6 Drawing Figures

MAPPING DISC DEFECT DETECTOR

BACKGROUND OF THE INVENTION

1. Field of the Invention

The present invention relates to the field of surface defect detection, and more particularly relates to the field of defect detection in planar surfaces, especially the surfaces of optical discs and related products.

2. Background Art

The development of optical discs and other high density recording media used for the recording and playback of video information has given rise to a need for very accurate defect detecting methods and apparatus. The optical disc, for example, contains stored information on the disc surface in the form of spiral tracks of optically readable indicia having dimensions and spacings of the order of approximately one micron. Defects in the surface of an optical disc, for example, tiny bumps or pits of even microscopic dimensions, can cause the interruption of signal recovery. However, because of their extremely small size such defects can easily escape detection by an unaided observer.

Consequently, apparatus have been devised for detecting such microscopic defects. Typically, such apparatus utilize a narrow beam of light, for example, a beam of laser light, which is imaged to a small spot on the disc and scanned across the disc, and then some property of the light which is reflected or scattered from the disc is detected. According to one such scheme, a histogram is automatically generated which correlates the sizes and numbers of surface defects detected in the surface of an optical disc.

However, it is desirable to know the precise location of defects on an optical disc, or like surface, in order to determine the physical pattern of occurrence of defects. Toward this end, it has been proposed to provide a videodisc on a rapidly spinning turntable that is translated under an imaged beam of laser light, to detect diffraction components generated thereby, and couple to the turntable a second turntable upon which is mounted a disc of electric recording paper. As defects are detected by the laser beam apparatus, marks are recorded on the paper, thus producing a map of the defects. A writing pen is used to record the marks on the paper.

A high-powered microscope is focused onto the disc at the spot where the laser light impinges on the disc. A low-powered microscope is focused on the tip of the writing pen where it contacts the paper. After the map is made, the leading edge of a mark on the recording paper is positioned under the low-powered microscope, to automatically bring the coupled primary turntable under the high-powered microscope and allow the selective observation of areas of the disc in which defects have been detected. While this scheme does propose to provide a map of defects on a videodisc, the use of a coupled secondary turntable and writing pen, limits the speed and response time of the system. Indeed, the marks recorded on the recording paper by such an apparatus take the form of tangential lines of considerable length. Where it is desired to have a map which provides an accurate depiction of the density of occurrance of dropouts, such a scheme provides limited resolution.

It is therefore desired to have apparatus capable of generating a map of defects in a disc, such as an optical disc, wherein such apparatus has rapid response so as to enable the generation of a map which accurately depicts the density of occurrence of defects on the disc. The present invention satisfies this need.

SUMMARY OF THE INVENTION

The present invention resides in apparatus for generating a map of detectable characteristics of a disc. A scanning signal display device, for example, a storage oscilloscope, is provided for displaying the map to be generated. A detector is coupled to the intensity input of the scanning signal display device for generating an electrical signal representative of the detectable characteristic at a pre-determined location in the disc. Relative motion is provided for the pre-determined location with respect to the disc such that the location is scanned in a spiral pattern. The relative motion between the location and the surface being scanned is detected and drive input signals are generated for the scanning signal display device such that the trace of the device follows a pattern corresponding to the spiral pattern of the pre-determined location.

The present invention is particularly adapted for use in connection with a high speed CRT type display device, for example a storage oscilloscope. High speed detectors and amplifiers can be used in the detecting circuitry as well as in the scanning circuitry for driving the CRT device to obtain a highly accurate map of the detected characteristics, limited primarily by the resolution of the screen of the CRT device. The present invention can be used in connection with a scanning apparatus which utilizes a motor driven rotating spindle to rotate the disc. Since the spindle motor need not be coupled to effect rotation of a secondary mechanical system, such as a secondary turntable, the spindle may be rotated at high speeds without concern for instabilities which might be induced because of coupling interactions. Further, due to the high frequency response of the display device and associated circuitry, the apparatus is capable of generating an accurate, high resolution map, even at high scanning rates. Consequently, detectable characteristic maps may be generated much more quickly as compared with prior art devices.

It will be appreciated from the foregoing that the present invention represents a significant advance in the field of defect detection. In particular, the invention provides a high speed and high resolution apparatus for generating maps of detectable characteristics, such as surface defects in discs. Other aspects and advantages of the present invention will become apparent from the following more detailed description, taken in conjunction with the accompanying drawings.

DETAILED DESCRIPTION OF THE PREFERRED EMBODIMENT

Figure 1A:
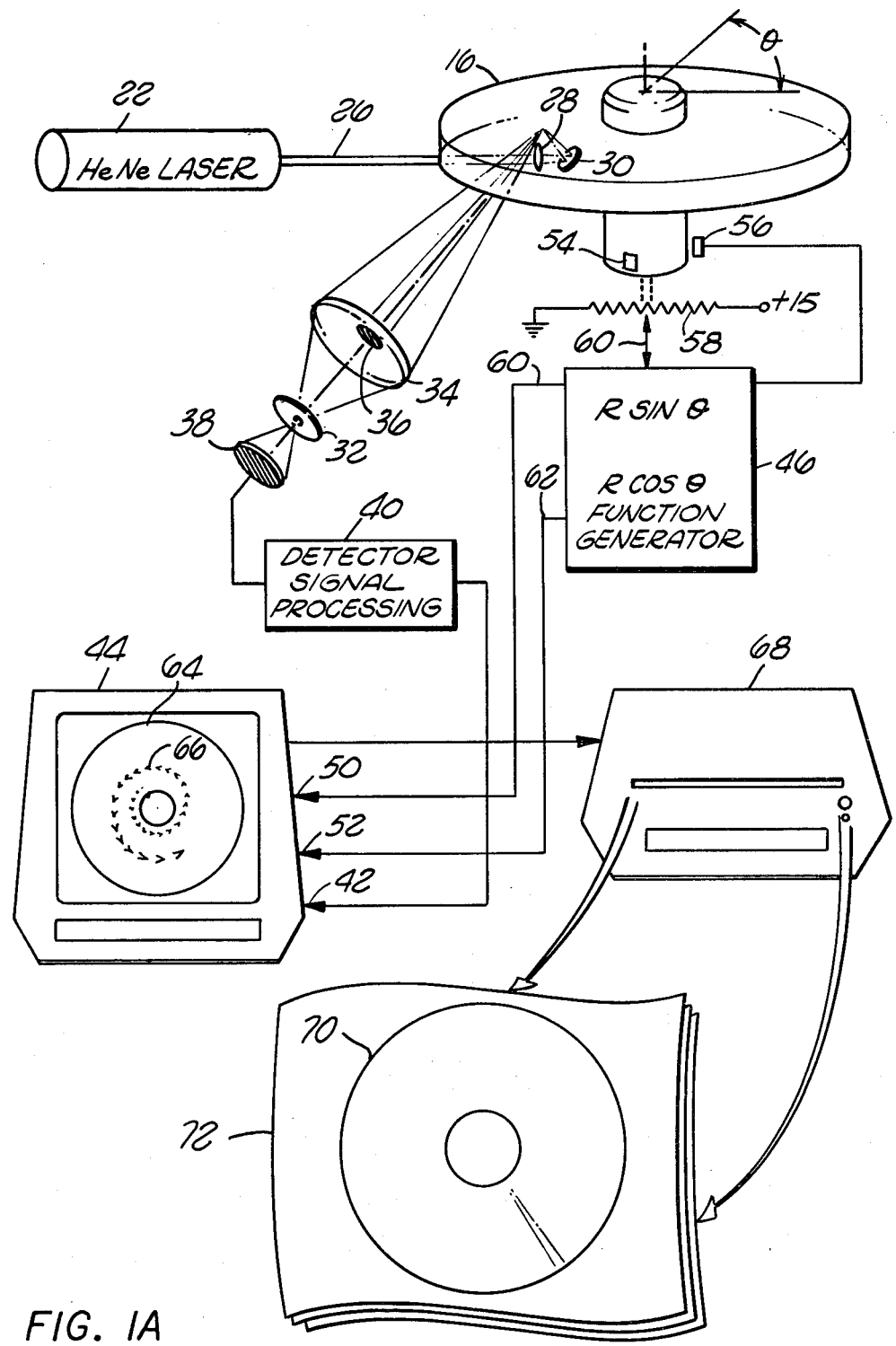
FIG. 1A is a schematic diagram of a defect detecting apparatus constructed according to the principles of the present invention.
Figure 1B:
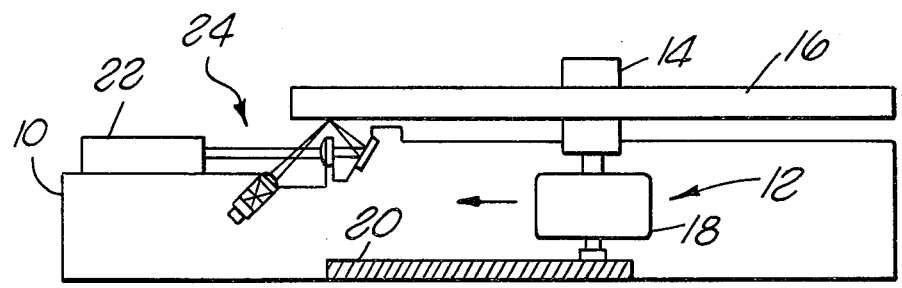
FIG. 1B is a cross section through a player apparatus modified in accordance with the principles of the present invention illustrating certain details thereof.

FIG. 1A is a schematic diagram of a defect detector mapping apparatus constructed according to the principles of the present invention. FIG. 1B is a cross-section through an apparatus incorporating the drive features of the system depicted in FIG. 1A illustrating certain details of the drive assembly thereof. FIGS. 1A and 1B depict an apparatus for detecting defects in a "glass master" 16. A glass master is a disc-shaped piece of high quality optical glass which is used in the optical disc manufacturing process.

The apparatus of FIGS. 1A and 1B can be constructed by modifying the design of a conventional optical disc player apparatus to account for the increased size and weight of the glass master 16 over an optical disc. FIG. 1B is a cross-sectional diagram through such a modified player apparatus 10. The drive system 12 for the apparatus 10 is utilized to provide rotational and translational motion to the spindle 14, and thus to the glass master 16 which is secured thereto. The drive system 12 comprises a constant rpm drive motor 18, and a conventional lead screw translation system 20. The player apparatus 10 is modified to support a laser 22 and optical system 24 which will be described in more detail below.

Turning now to FIG. 1A, a helium neon laser 22 is provided which emits a beam 26 of laser light which passes through a focusing lens 28. After being reflected by a mirror 30 the beam 26 of laser light converges to a spot on the lower surface of the glass master 16. The beam 26 is reflected off the lower surface of the glass master 16 and is directed to a second focusing lens 34 which is provided with a circular mask 36 which blocks all of the light reflected by mirror reflection from the lower surface of glass master 16. Components of light other than pure reflection components pass through the secondary lens 34 and are focused to a photodetector 38 through a small aperture in a field stop 32.

The output of photodetector 38 is applied to a detector signal processing circuit 40. Signals from photodetector 38 having desired threshold magnitude and duration characteristics cause the processing circuit 40 to generate output signal pulses which are applied to the intensity, or "Z-Axis" input 42 of a conventional storage oscilloscope 44.

An R sin $\theta$ and R cos $\theta$ function generator 46 generates signals which are applied to the X-Axis deflection input 50 and the Y-Axis deflection input 52 of the storage oscilloscope 44. The function generator 46 is provided with a single pulse every rotation of the glass master 16, from an assembly comprising a mirror 54 mounted on the shaft of the spindle and a Source and Sensor Optical Electric Module 56 assembly, for example, Texas Instruments type TIL149. The mirror 54 is mounted with respect to the module 56 such that with every revolution of the spindle the mirror passes through the path of the radiation emitted by the module 56, thereby reflecting the radiation back to the sensor portion of the module 56, which in response produces a pulse.

A potentiometer 58 is connected between ground and a 15 volt source of electrical potential. The wiper arm 60 of the potentiometer 58 is coupled to the linear translation assembly of the drive system which is discussed below. Translation of the spindle causes the wiper arm 60 of potentiometer 58 to move, and this gives rise to a varying voltage on wiper arm 60. This voltage, which is representative of the linear position of the glass master 16 within its range of translation, is applied to an input of the function generator 46.

One output 60 of function generator 46 is applied to the X-Axis deflection input 50 of the storage display device 44. The other output 62 of function generator 46 is applied to the Y-Axis deflection input 52 of display device 44. The function generator 46 generates output signals which, acting in conjunction, provide deflection signals for the display device 44 which cause the trace of the device 44 to track in a spiral corresponding to the path of the imaged spot of laser light 26 on the bottom surface of the glass master 16.

Since the output of the detector signal processing circuit 40 is connected to the Z-Axis input of the device 44, the trace of the device 44 generates a map of the characteristics detected by the photo-detector 38 and discriminated by processing circuit 40. Because the device 44 is a storage oscilloscope, the map 66 can be preserved on the screen for later reference. For example, once an entire map 66 has been constructed a photograph may be taken of the screen to preserve the map as a record.

The storage oscilloscope display device 44 is also coupled to a "hard copy" unit 68 which, when activated produces a map 70 on paper 72, corresponding to the map 66 produced on the screen 64 of the display device 44.

Figure 2:
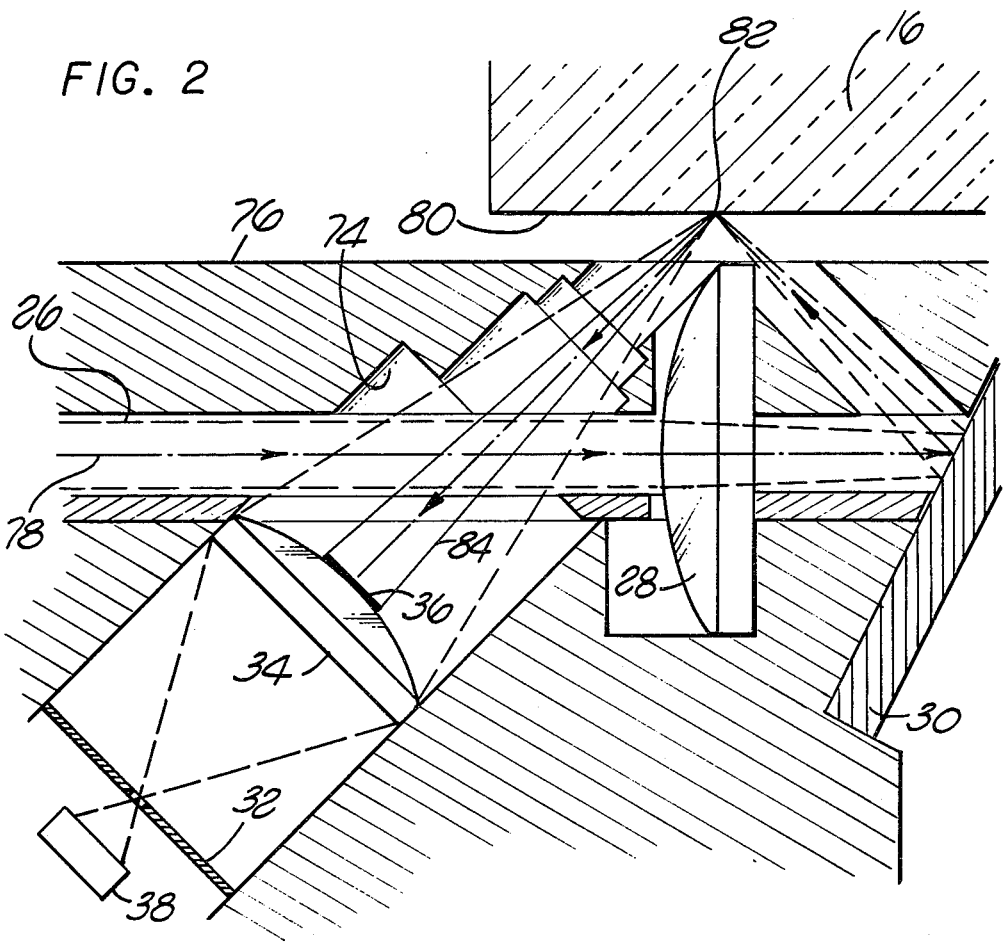
FIG. 2 is a cross-section view showing the details of a portion of the optics of the system shown in FIG. 1B.

FIG. 2 is a cross-sectional diagram through apparatus 10 depicting in more detail the major elements of the optical system 24 shown in FIG. 1A and 1B. The path of the beam 26 of laser light is confined within cavaties 74 in the base material 76 of the apparatus 10 (FIG. 1B). This reduces the risk of inadvertent exposure of a user of the apparatus to the beam of laser light 26. It also serves to prevent unwanted spurious components of light from reaching the photodetector 38 of the optical system.

In the view of FIG. 2 the beam 26 of laser light enters from the left, parallel to the lower surface 80 of the glass master 16, and passes through primary lens 28. The beam 26 continues through lens 28 to a mirror 30 which is oriented at an angle of approximately $22\frac{1}{2}°$ with respect to the central axis 78 of the beam 26 of laser light. The light beam 26 is thereby directed up to the lower surface 80 of the glass master 16 at an angle of 45°. The position of the lens 28, mirror 30 and glass master 16 are selected so that the beam 26 of laser light is imaged to a tiny spot at the lower surface 80 of the disc 16. The light beam 26 is reflected and scattered from the lower surface 80 of the glass master 16. Most of the light is reflected in mirror reflection from the surface 80, and is therefore directed from the surface 80 in a narrow cone 84 of light.

The presence of a defect on the surface 80 at the point 82 where the beam 26 impinges on the surface 80 gives rise to scattering components of light which occupy a volume outside the cone 84 of reflection component light. The dispersion angle of these scattering components depends upon the size of the defect which produces them, the smaller the defect the larger the dispersion angle of the scattering components produced thereby. The cone 84 of reflected light impinges on the occulting patch 32 where it is absorbed. The occulting patch 36 is preferably a circular piece of absorptive material, such as dull black construction paper, which is attached to the secondary lens 34 as by glueing.

Those scattering components outside of the cone 84 of reflected light and inside a cone 86 defined by the point 82 and the periphery of the secondary lens 34 pass through the secondary lens 34 and are focused to a small spot within the aperture 31 of the field stop 32. The field stop blocks components of light which do not have spot 82 as their source, and which are therefore unwanted, for example, reflection components from within the glass master. The photodetector 38 detects the light passing through the aperture 32.

The exact dimensions and parameters of the various components just described in connection FIG. 2 are largely a matter of choice for the designer according to the particular application. In an embodiment which was actually constructed, a helium neon laser was used as the laser source and a twenty five millimeter focal length lens selected for the primary lens 28. A thirty millimeter focal length lens was selected for the secondary lens 34 and was placed at a distance of approximately twenty millimeters from the point 82 of impingement on surface 80. A one millimeter diameter occulting patch 36 was placed on the secondary lens 34. A one hundred micron diameter hole formed aperture 32.

Figure 3:
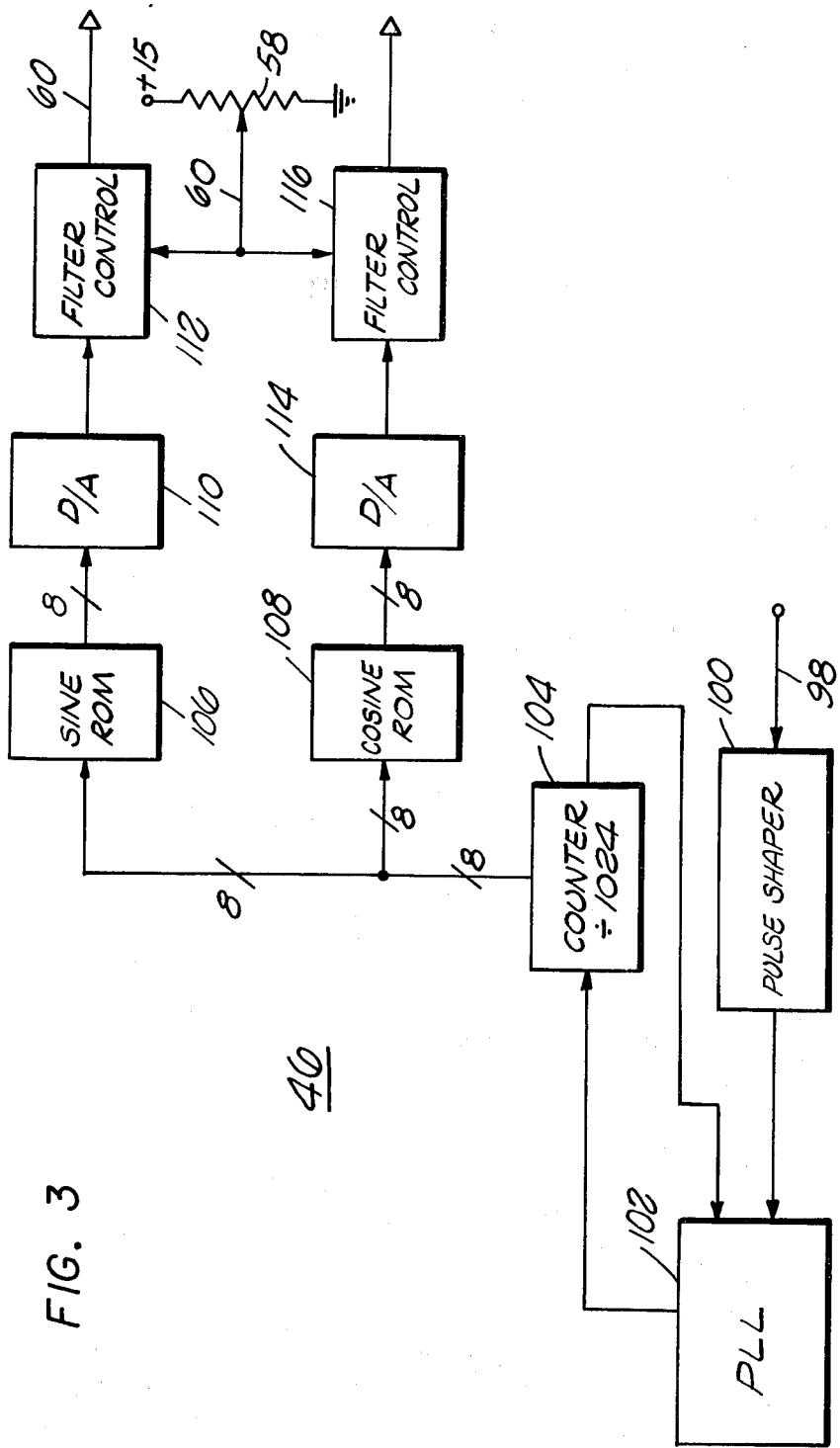
FIG. 3 is a block diagram of drive circuitry utilized in connection with the system shown in FIG. 1.

FIG. 3 is a block diagram of an R sine $\theta$ and R cosine $\theta$ function generator 46. The circuit includes a pulse shaper 100 connected to the output of the spindle rotation detector 56 (FIG. 1A). The output of the pulse shaper 100 is connected to a phase locked loop ("PLL") 102 set to oscillate at a rate of 1024 times the repetition rate of the pulses on line 98. The output of PLL 102 is applied to the input of a divide-by-1024 counter 104. The eight bit parallel line output 106 of counter 104 is applied both to a sine function ROM 106 and to a cosine function ROM 108. The output of the sine function ROM 106 is connected to a first digital-to-analog converter 110, the output of which is connected to a first low pass filter and amplitude control 112. The output of the filter/control 112 is applied to line 60 which, it will be recalled, is connected to the X-Axis drive input of display device 44 (FIG. 1A). The output of the cosine function ROM 108 is connected to a second digital-to-analog converter 114, the output of which is connected to a second low pass filter and amplitude control 114. The output of filter/control 114 is applied to line 62 which is connected to the Y-Axis drive input of display device 44 (FIG. 1A).

Digital-to-analog convertors 110 and 114 convert the digital output of ROMs 106 and 108 respectively, into corresponding analog values. The filter/control circuits 112 and 116 filter the unwanted high frequency components of the output of digital-to-analog convertors 110 and 114, respectively, and control the amplitude of the sine and cosine waveforms output therefrom in accordance with the position of the wiper arm 60 on potentiometer 58 (FIG. 1A).

The ROMs 106 and 108 are standard commercial devices and each may be, for example, a 2048 X 8-bit EPROM, such as a MOSTEK MK2716(T) 16K-bit EPROM. Storage locations having addresses zero through 1023 in the ROM 106 are programmed sequentially with digital values corresponding to the amplitude values of a sine function at 1024 equally spaced sample locations of the waveform. Likewise, ROM 108 is loaded the sample values of a cosine function waveform.

In operation, the pulse shaper 100 receives on line 78 a train of pulses at a repetition rate equal to the rotation rate of the glass master 16. The pulse shaper 100 buffers these pulses and puts them in the form of rectangular pulses suitable for processing by PLL 102. As mentioned previously, PLL 102 is set to oscillate at a frequency equal to 1024 times the repetition rate of the pulses on line 78. The PLL 102 "locks up" with the pulses outputted by the pulse shaper 100, thereby causing the output of counter 104 to be in synchronization with the pulses on line 98. Thus, the counter 104 counts up cyclically and synchronously in binary from 0 to 1023 every time a pulse is received on line 98.

As the counter 104 counts up from zero, storage locations in ROMs 106 and 108 having addresses corresponding to the count output of counter 104 are accessed. As the contents of the storage locations are accessed they are outputted to the respective digital to analog convertors 110 and 114. Because of the cyclic nature of sine and cosine function waveforms, as the counter 104 counts cyclically from 0 to 1023 so the outputs of sine function ROM 106 and cosine function ROM 108 cycle through digital values corresponding to a continuous sine function and cosine function, respectively. In turn, the outputs of digital to analog convertors 110 and 114 represent the analog waveform equivalents of the digital values applied to their respective inputs. These waveforms are in synchronization with, and in a substantially constant phase with respect to the pulse input on line 98 and, hence, to the rotation of the glass master 16 (FIG. 1A).

The filter/control circuits 112 and 116 vary the amplitudes of the respective signals applied thereto linearly and in the same amount in accordance with the position of the wiper arm 60 of potentiometer 58. This causes the display device 44 (FIG. 1A) to generate a spiral trace corresponding to the pattern traced by the spot of light from the laser on the lower surface of the glass master 16.

The components represented by blocks in FIG. 3 and described above are each separately known circuits comprised of commercially available components. For example, PLL 102 is a standard phase locked loop which can, for example, be built around a Signetics 565 package. Further, for example, the amplitude adjusting portion of the low pass filter and amplitude adjusting circuits 112 and 116 can be a standard analog multiplier integrated circuit.

The circuit depicted in FIG. 3 is considered preferred because it provides appropriate X and Y Axis drive signal outputs for a storage display device which are accurate over a wide range of frequencies of input pulses on line 98 (FIG. 3). Other circuits can readily be designed and utilized by one with ordinary skill in the art based on the principles of the present invention disclosed herein. For example, if it is known that the work piece being inspected rotates at a fixed rate, a simpler and less costly circuit, described below, can be designed utilizing a one shot to generate a 50% duty cycle signal.

Figure 4:
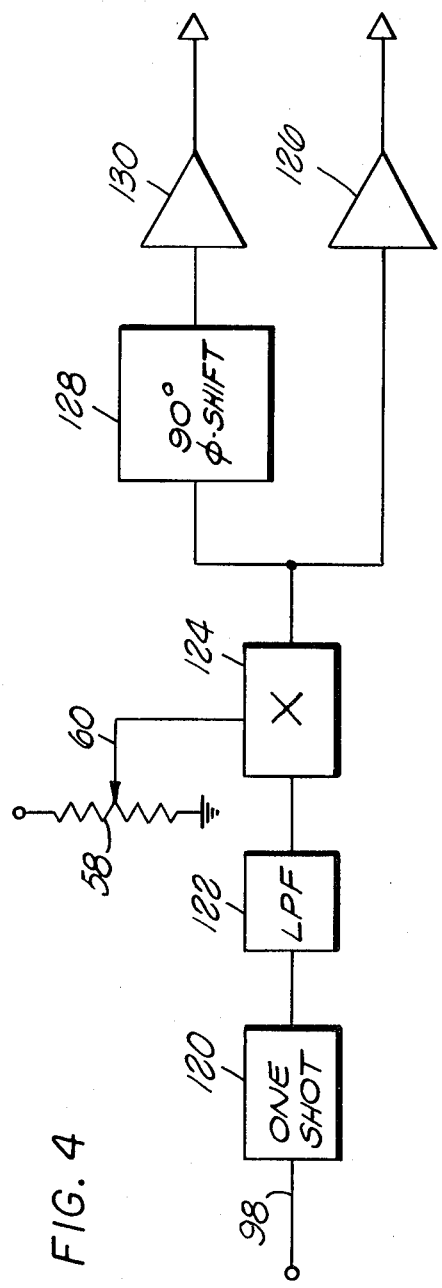
FIG. 4 block diagram of an alternative drive circuit for driving the display device of FIG. 1A.

FIG. 4 is a block diagram of such a simplified circuit. In this embodiment the input line 98 from the spindle rotation detector 56 is applied to the input of a controllable one shot 120. The pulse duration of one shot 120 is set to exactly one half of the repetition frequency of the pulses on line 98. The output of one shot 120 is therefore a square wave at the frequency of the pulses on line 98 and, hence, of the frequency of rotation of the glass master 16 (FIG. 1A). The output of one shot 120 is applied to low pass filter 122 which filters out the high frequency components of the square wave output from one shot 120 and converts the waveform into a sinusoid. The output of low pass filter 122 is applied to one input of an analog multiplier 124. The other input of multiplier 124 is connected to the wiper arm 60 of the radial position potentiometer 58 (FIG. 1A).

The output of multiplier 124 is applied to a driver amplifier 126 and to a 90° phase shifting circuit 128. The 90° phase shifting circuit 128 outputs a signal waveform substantially identical to its input waveform but shifted by 90° in phase. Where the frequency of the input waveform is constant and known, the 90° phase shifting circuit 128 can be a simple RC network, for example, connected to an amplifier to compensate for the decrease in amplitude at the 90° phase shift point. The output of phase shifting circuit 128 is applied to a second amplifier 130. The outputs of amplifiers 126 and 130 are related to one another, therefore, as sine to cosine. These outputs may be used to drive the X and Y Axis inputs of display device 44 (FIG. 1A).

Figure 5:
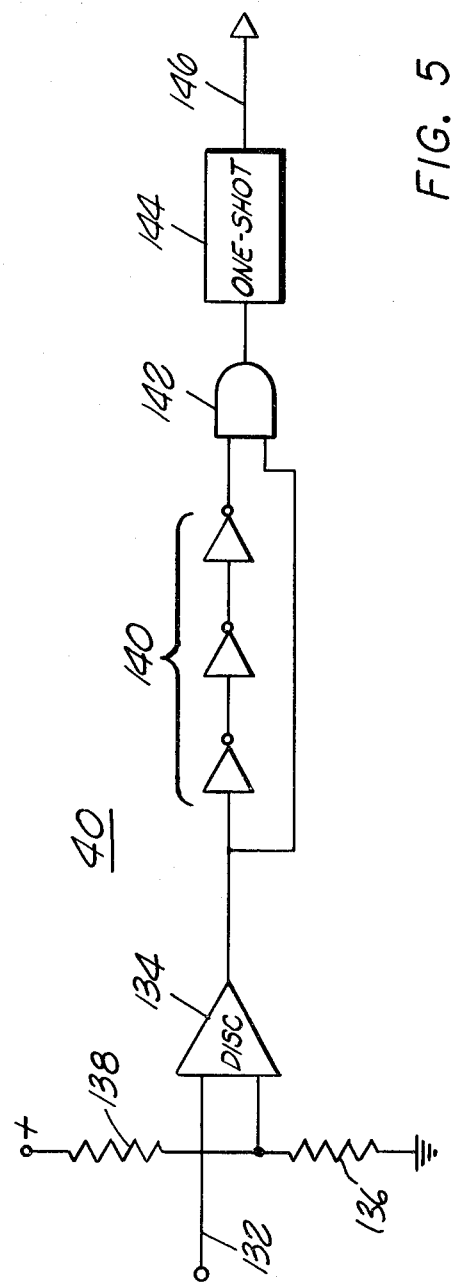
FIG. 5 is a circuit diagram of the detector signal processing circuit of FIG. 1A.

FIG. 5 is a block diagram of the detector signal processing circuit 40 of FIG. 1A. The output of detector 38 is applied to processing circuit 40 by way on an input line 132. Line 132 is connected to the input of a comparator circuit 134. A voltage divider, comprising resistors 136 and 138 connected between a reference voltage and ground, determine the threshold voltage for comparator 134. The output of comparator 134 is connected to a delay line 140 and to one input of an AND gate 142. The output of the delay line 140 is connected to the other input of AND gate 142. The output of AND gate 142 is connected to the input of a one shot 144, the output of which is connected to a line 146. Line 146 is connected to input 42 of the display device 44 (FIG. 1A).

In operation, signal voltages on line 132 exceeding the threshold voltage level set for comparator 134 result in a positive signal at the output of comparator 134. This positive signal is applied to the delay line 140 and to AND gate 142 which together act as a duration discriminator. Only pulses exceeding the delay time of the delay line 142 cause a positive signal at the output of AND gate 142. One shot 144 ensures that any signal appearing on line 132 which exceeds these signal amplitude and duration thresholds results in the production of a pulse having sufficient duration to produce a visible trace on the screen of the display device 44 (FIG. 1A). The amplitude and duration thresholds are selected according to the desire of the user. The timing of one shot 144 is determined by the characteristics of the display device.

Although the invention has been described in detail with reference to its presently preferred embodiment, it will be understood by one of ordinary skill in the art that various modifications can be made without departing from the spirit and scope of the invention. For example, other characteristics than surface irregularities in glass masters can be detected and mapped according to the present invention. Signal drop-outs in the playback of video optical discs can be mapped, as can surface irregularities and track spacing deviations outside of a defined range in such discs. Apparatus for detecting such characteristics which employ spiral tracking techniques have been devised. Knowing the principles of the present invention disclosed herein, such apparatus can be combined using ordinary skill in this art with circuitry or other means for generating drive input signals for a scanning signal display device and a suitable map of such characteristics can be obtained thereby. Accordingly, it is not intended that the invention be limited, except as by the appended claims.

We claim:

1. Apparatus for generating a map of detectable characteristics of a rotatable disc, comprising:
   a scanning signal display device;
   detecting means for examining a small fraction of the disc at a time, said detecting means generating a first electrical signal coupled to the intensity input of said scanning signal display device, said signal being representative of a detected characteristic of the disc in the fraction of the disc being examined;
   scanning means for moving the disc relative to said detecting means such that said detecting means examines the disc in a spiral pattern, said scanning means including a spindle for holding the disc, means for rotating said spindle, and means for translating said spindle relative to said detecting means;
   pulse generator means for generating a rotation pulse signal each complete rotation of said spindle;
   variable signal means for generating a translation signal which varies in accordance with the translational position of said spindle; and
   function generator means coupled to said pulse generator means and to said variable signal means for generating a first sinusoidal output signal and a second sinusoidal output signal, each at a frequency proportional to the frequency of said rotational pulse signal and each having an amplitude proportional to the value of said translation signal, said signals differing in phase by 90°, said first and said second sinusoidal output signals being coupled to said scanning signal display device such that the trace of said device follows a spiral pattern corresponding to the position of said detecting means relative to the disc.

2. Apparatus according to claim 1 wherein said detecting means comprises a laser beam defect detector, including a photodetector for producing said first electrical signal.

3. Apparatus according to claim 2 wherein said detector means further comprises signal processing means for producing a second electrical signal only if said first electrical signal exceeds a predetermined threshold amplitude.

4. Apparatus according to claim 3 wherein said signal processing means further comprises means for causing said second electrical signal to be produced only when said first electrical signal exceeds a predetermined duration at said predetermined threshold amplitude.

5. Apparatus according to claim 1 wherein said function generator means comprises:
   address means coupled to said pulse generator means for generating a cyclically recurring series of sequential digital signals in synchronization with said rotation pulses;
   first and second addressable memory means coupled to said address means having sinusoidal function sequential sample values stored therein at sequentially addressed storage locations, such that said second memory means sinusoidal function differs by 90° in phase with said first memory means sinusoidal function;
   first and second digital to analog converter means coupled to the outputs of said first and second addressable memory means, respectively; and
   amplitude control means coupled to said variable signal means for simultaneously controlling the amplitude of the outputs of said first and second digital to analog converter means in accordance with said translation signal.

* * * * *